US010353996B2

(12) United States Patent
Bellamy et al.

(10) Patent No.: US 10,353,996 B2
(45) Date of Patent: Jul. 16, 2019

(54) AUTOMATED SUMMARIZATION BASED ON PHYSIOLOGICAL DATA

(71) Applicant: INTERNATIONAL BUSINESS MACHINES CORPORATION, Armonk, NY (US)

(72) Inventors: Rachel Bellamy, Bedford, NY (US); Victor C. Dibia, Yorktown Heights, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 125 days.

(21) Appl. No.: 15/424,997

(22) Filed: Feb. 6, 2017

(65) Prior Publication Data

US 2018/0225271 A1 Aug. 9, 2018

(51) Int. Cl.

| G06F 17/27 | (2006.01) |
|---|---|
| G06F 17/24 | (2006.01) |
| A61B 5/16 | (2006.01) |
| G10L 15/26 | (2006.01) |
| G06F 16/34 | (2019.01) |
| A61B 5/00 | (2006.01) |
| A61B 5/01 | (2006.01) |
| A61B 5/053 | (2006.01) |
| A61B 5/021 | (2006.01) |
| A61B 5/08 | (2006.01) |
| A61B 5/024 | (2006.01) |
| A61B 5/145 | (2006.01) |

(52) U.S. Cl.
CPC ............ *G06F 17/241* (2013.01); *A61B 5/165* (2013.01); *G06F 16/345* (2019.01); *G10L 15/26* (2013.01); *A61B 5/01* (2013.01); *A61B 5/021* (2013.01); *A61B 5/024* (2013.01); *A61B 5/0531* (2013.01); *A61B 5/0816* (2013.01); *A61B 5/14542* (2013.01); *A61B 5/681* (2013.01); *A61B 2503/12* (2013.01)

(58) Field of Classification Search
None
See application file for complete search history.

(56) References Cited

U.S. PATENT DOCUMENTS

| 7,444,285 | B2 * | 10/2008 | Forbes | G10L 15/26 |
|---|---|---|---|---|
| | | | | 379/88.01 |
| 9,251,809 | B2 * | 2/2016 | Reiner | G10L 25/48 |
| 9,292,576 | B2 * | 3/2016 | Biem | G06F 17/30516 |
| 2004/0204635 | A1 * | 10/2004 | Scharf | A61B 5/0002 |
| | | | | 600/323 |
| 2007/0071206 | A1 * | 3/2007 | Gainsboro | H04M 3/2281 |
| | | | | 379/168 |

(Continued)

*Primary Examiner* — Satwant K Singh
(74) *Attorney, Agent, or Firm* — F. Chau & Associates, LLC (57) ABSTRACT

A computer-implemented method for generating an automated summary of a document based on physiological data annotation includes receiving a textual transcript, by a computer. Physiological data is received from one or more devices. Passages of the textual transcript are scored based on received physiological data. A summary of the textual transcript is automatically created, in response to said scoring passages of the textual transcript. Other embodiments include a system and a computer program product.

17 Claims, 4 Drawing Sheets

(56) References Cited

U.S. PATENT DOCUMENTS

| | | | |
|---|---|---|---|
| 2009/0089100 A1* | 4/2009 | Nenov | G06Q 50/22 |
| | | | 705/3 |
| 2011/0245633 A1 | 10/2011 | Goldberg et al. | |
| 2012/0239435 A1* | 9/2012 | Ennett | G06F 19/325 |
| | | | 705/3 |
| 2013/0211265 A1* | 8/2013 | Bedingham | G06F 19/3418 |
| | | | 600/483 |
| 2014/0363797 A1 | 12/2014 | Hu et al. | |
| 2017/0039480 A1* | 2/2017 | Bitran | G06F 19/3481 |
| 2017/0068792 A1* | 3/2017 | Reiner | G06F 19/3406 |

* cited by examiner

AUTOMATED SUMMARIZATION BASED ON PHYSIOLOGICAL DATA

BACKGROUND

The present invention relates to automated summarization and, more specifically, to automated summarization based on physiological data annotations.

Automated summarization techniques may be used to summarize a document. However, such automated summarization techniques can fail to achieve awareness of and/or reflect context and other cues that facilitate human understanding of language.

SUMMARY

A computer-implemented method for generating an automated summary of a document based on physiological data annotation includes receiving a textual transcript, by a computer. Physiological data is received from one or more devices. Passages of the textual transcript are scored based on received physiological data. A summary of the textual transcript is automatically created, in response to said scoring passages of the textual transcript. Other embodiments include a system and a computer program product.

BRIEF DESCRIPTION OF THE SEVERAL VIEWS OF THE DRAWINGS

A more complete appreciation of the present invention and many of the attendant aspects thereof will be readily obtained as the same becomes better understood by reference to the following detailed description when considered in connection with the accompanying drawings, wherein.

DETAILED DESCRIPTION

In describing exemplary embodiments of the present invention illustrated in the drawings, specific terminology is employed for sake of clarity. However, the present invention is not intended to be limited to the illustrations or any specific terminology, and it is to be understood that each element includes all equivalents.

By way of overview, exemplary embodiments of the present invention relate to a system, method and computer program product for capturing physiological data from wearable devices, such as one or more biometric sensors worn by a human consumer of a presentation or text transcript. The captured physiological data can be interpreted and the interpretations annotated onto the textual transcript. If the presentation is oral, it can be first converted using conventional speech-to text technology. The annotated text can then be scored based on the physiological interpretations. Automated summarization of the textual transcript may then utilize these scores to summarize of the textual transcript.

Automated summarization techniques, according to exemplary embodiments of the present invention, may be used to create a concise textual summary from a larger textual document by identifying portions of the larger textual document that appear to be of elevated significance. Approaches for automated summarization may utilize extraction or abstraction. Extactive approaches may work by selecting a subset of existing words, phases, or sentences from the original text and use that selected subset as a summary. Abstractive approaches may build an internal semantic representation and then use natural language generation techniques to create a summary that may contain words not explicitly present in the original text.

While exemplary embodiments of the present invention are described herein in terms of performing automated summarization on a textual transcript, the present invention is not limited to this particular task or material. By way of example only, embodiments of the present invention may be applied to generate an automated summary of other materials, e.g., such as recorded event traces, media repositories generated based on large repositories of human activity, and other large and/or complex data sets.

Thus, the term textual transcript should be interpreted to encompass all such materials. Such textual transcripts, event traces, media repositories, and other large data sets may be too lengthy and/or complex for humans to be reasonably expected to be able to summarize. By way of example only, materials can include tens or hundreds of thousands of pages of information, so that computational tools for automated summarization may be increasingly relied upon to convert these large data sets into concise summaries that are able to be processed by the human mind, thereby giving readers an opportunity to understand even the largest of datasets.

Exemplary embodiments of the present invention may utilize physiological data from human observers in scoring concepts found within the textual transcripts. This physiological data may be acquired from one or more individuals providing the text (e.g. presenters) and/or from one or more individuals watching the presentation of the text (e.g. participants). The physiological data may be captured both at a distance, for example, using audio/video recording equipment, and by contact, for example, using the aforementioned wearable devices that include one or more biometric sensors.

Figure 1:
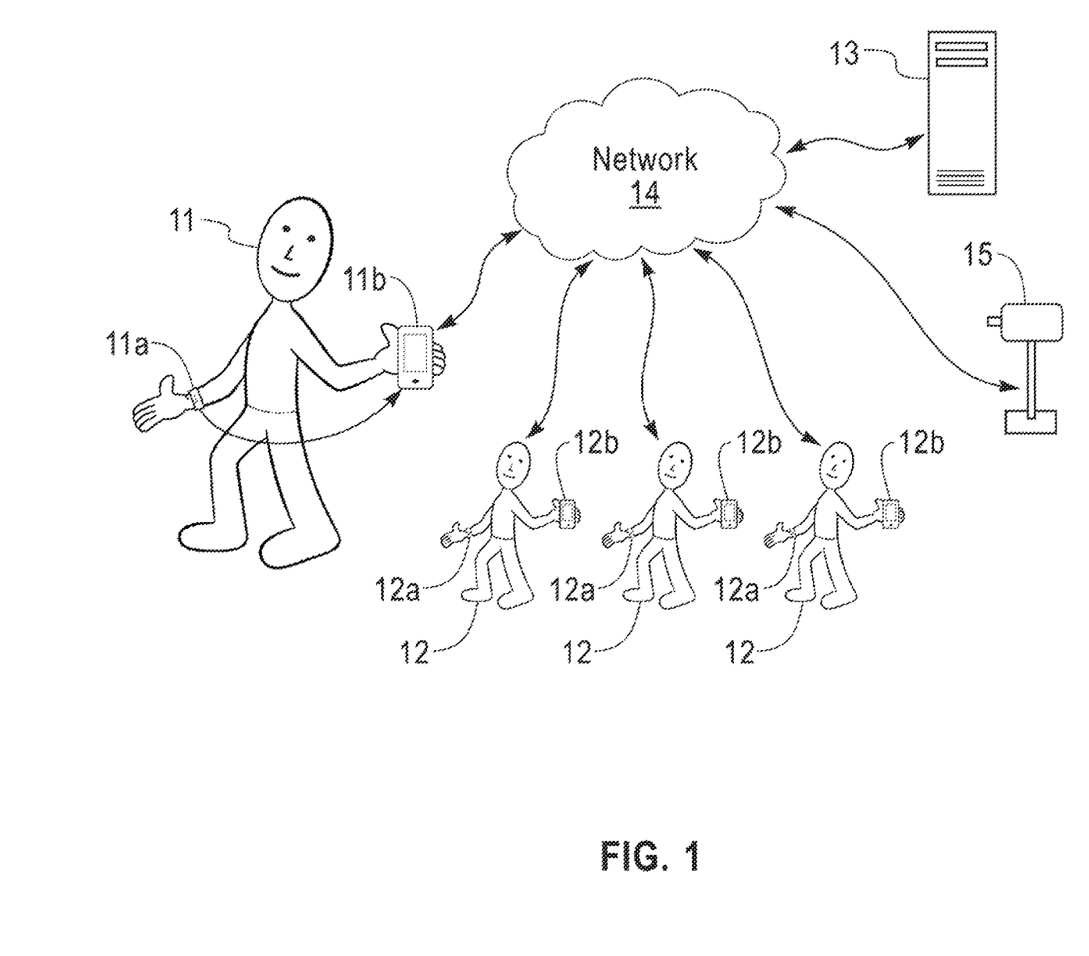
FIG. 1 is a diagram illustrating a system in accordance with exemplary embodiments of the present invention.

FIG. 1 is a diagram illustrating a system for performing automated summarization based on physiological data annotations according to exemplary embodiments of the present invention. As depicted, the system may include a plurality of wearable devices 11a and 12a. For example, a presenter 11 may be wearing wearable device 11a and multiple participants 12 may each be wearing wearable devices 12a. A more detailed example of a wearable device will be described below with respect to FIG. 3.

In some embodiments of the present invention, only the participants 12 may be wearing wearable devices 12a. In some embodiments of the present invention, neither the presenter 11 nor all participants 12 wear the wearable devices and the applicable physiological data is captured from a distance, e.g., via one or more remote devices. By way of example only, as depicted in FIG. 1, physiological data may be captured at a distance by audio/video equipment 15, such as a microphone and/or video camera. By way of further example, in some embodiments—if teleconference equipment is available in a conference room—teleconference equipment may be used as the microphone and/or video camera. Other (non-limiting) examples of suitable audio/video equipment 15 include webcams, security cameras, videophones, and the like. Other (non-limiting) examples of devices that can be used for remote capture of physiological data include: temperature scanners, humidity sensors, and odor detectors such as may be implemented by chemosensors, gas chromatagtaphy sensors, mechanical sensors and other devices.

Regardless of whether the physiological data is captured locally, e.g., by a wearable device or remotely, e.g., through remote sensors, the captured physiological data may be used to assist in the measurement of participant 12 and/or presenter 11 reactions to material. For example, captured physiological data may be used to assist in the measurement of otherwise externally imperceptible emotional reactions to a presentation, and/or to measure an emotional reaction of the him/herself.

A few (non-limiting) examples of physiological data that may be acquired include: body temperature, skin conductivity, heart rate (e.g. pulse), blood pressure, neural oscillations, blood oxygen levels, respiration rate, pheromones, etc. However, this list is not exhaustive, and it is to be understood that other physiological data may be detected/acquired by either biometric sensors incorporated into a wearable device or other sensors that acquire physiological data at a distance, either for individuals (e.g. the presenter 11 and the participants 12) or for a group of people.

Referring again to FIG. 1, the audio/video recording equipment 15 may be in communication with a central server 13, for example, over an electronic network 14. The central server 13 may include one or more server devices, located in proximity to the audio/video recording equipment 15 or remotely. The electronic network 14 may include a wireless network, a local area network (LAN), and/or a wide area network (WAN), such as the Internet.

In some embodiments, the presenter 11 and/or one or more participants 12 may also carry smartphone devices 11b/12b that may be in communication with corresponding wearable devices 11a/12a. In some embodiments, the smartphone devices 11b/12b are adapted to receive physiological data from the corresponding wearable devices 11a/12a and communicate the physiological data to the central server 13, for example, over the electronic network 14. Alternatively, the wearable devices 11a/12a may communicate directly with the central server 13 over the electronic network 14.

Figure 2:
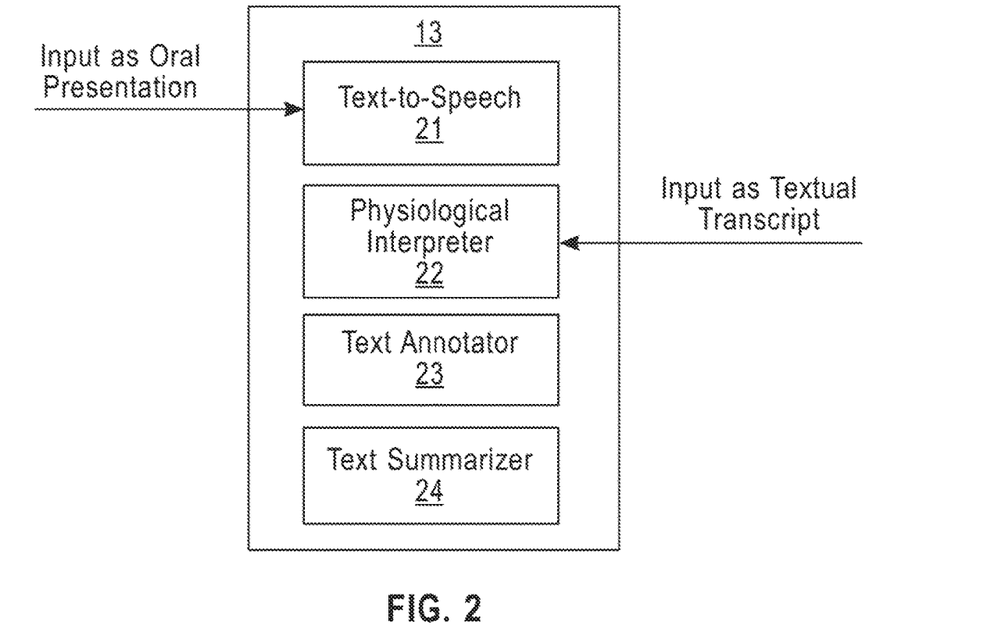
FIG. 2 is a schematic diagram illustrating a more detailed example of the server (depicted in FIG. 1) in accordance with exemplary embodiments of the present invention.

FIG. 2 is a schematic diagram illustrating a more detailed example of central server 13 in accordance with some embodiments of the present invention. As described with reference to FIG. 1, the central server 13 may include one or more computational devices. By way of example only, such an organization can facilitate distribution of a central server 13 processing load. In another (non-limiting) example, the central server 13 may be embodied as a virtual machine (VM) executing on a partition of a remote computational device along other VM partitions that provide other functions. Regardless of how central server 13 is organized, it may include various modules for performing specialized processing tasks. In some embodiments, one or more such modules are instantiated as program instructions executing on server 13.

Referring now specifically to the example depicted in FIG. 2, modules 21-24 include a text-to-speech module 21, a physiological interpreter module 22, a text annotator module 23, and a text summarizer module 24.

The text-to-speech module 21 is configured to receive orally presented material and converting that speech into a textual transcript. By way of example only, in some embodiments, the text-to-speech module 21 may be omitted (or not invoked) e.g., in embodiments where the material is directly received in text form.

The text-to-speech module 21 may also timestamp the textual transcript so that the specific time a word or phrase segment of an oral presentation was presented may be known from the timestamp information.

A physiological interpreter module 22 receives the physiological data and can interpret the physiological data as one or more emotional responses to a particular segment of the material. In one example, the physiological interpreter module 22 may (binarily) tag moments of heightened emotional excitement/engagement via setting a binary flag "0" or "1" value. However, in some embodiments, the physiological interpreter module 22 may interpret physiological data as corresponding to one or more of several gradations of emotional responses and may also interpret their relative strength. The physiological interpreter module 22 may also timestamp these interpretations.

In some embodiments, physiological interpreter module 22 may utilize a rules database to determine how to interpret various different physiological data profiles (not depicted). Alternatively, computer learning technology may be used to train emotional classifiers to perform a physiological interpretation. In this case, the emotional classifiers may be trained with training data, which may include supplemental data provided by the presenter 11 and/or the participants 12 describing their emotional mood at points in time. For example, the participants 12 may provide such data by responding to questions posed via their smartphones 12b as the presentation is delivered.

A text annotator module 23 may receive the physiological interpretations provided by physiological interpreter module 22 and use them to annotate the textual transcript e.g., converted by the text-to-speech module 21, for example, by matching time stamps. By way of example only, in some embodiments, the text annotator module 23 may be omitted as the physiological interpreter 22 may be responsible for annotating the textual transcript.

A text summarizer module 24 may take the annotated textual transcript and may automatically summarize the annotated textual transcript using the annotations. For example, the text summarizer module 24 may use the annotations to assign an engagement score to one or more passages of the textual transcript, where "passage" includes any segment or portion of text e.g., a single term/word, phrase, sentence, paragraph, etc. For example, a higher score may be assigned to a passage that corresponds to a high level of emotional engagement from a large number of people. A lower score may be assigned to a passage that corresponds to low levels of emotional engagement from a majority of people.

Where the emotional engagement of the presenter 11 is tracked, the scoring may rate the emotional engagement of the presenter 11 higher than that of one or more individual participants 12. For example, the emotional engagement of the presenter 11 may be given equal weight to the average emotional engagement of all participants 12 in calculating the score of each passage.

The scores assigned to each passage may then be used in performing the automatic summarization so that highly scored passages are more likely to influence the summary than passages that are low-scored.

The importance scores, so calculated, may be used to seed machine learning algorithms that can be used in text summarization.

The text summarizer 24 may output the automatically generated summary, for example, to a display unit or some other form of output. It is to be understood that while exemplary embodiments of the present invention have focused on automatically summarizing a textual transcript with a textual summary, exemplary embodiments of the present invention may also be applied to other forms of summaries. For example, the presentation may be recorded as an audio/video file, and the summary may include excepts of the audio/video recording.

Figure 3:
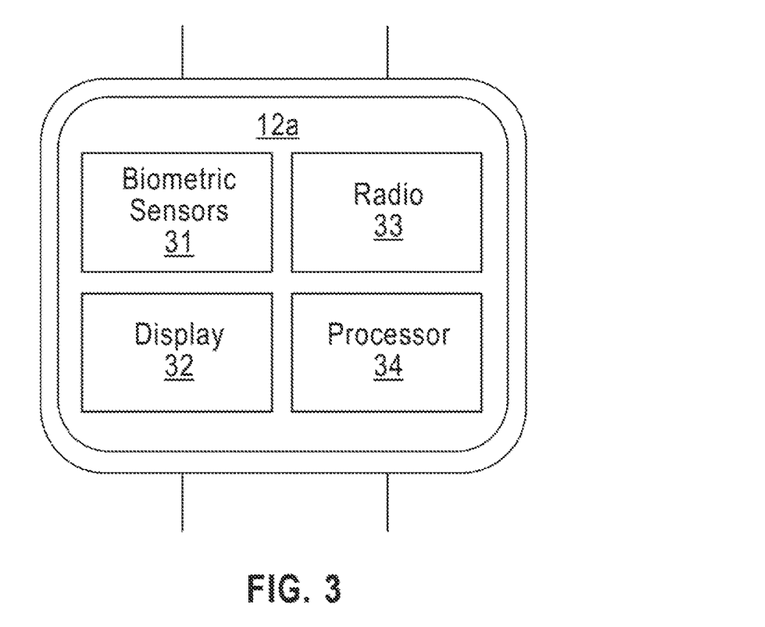
FIG. 3 is a schematic diagram illustrating a more detailed example of the wearable device (depicted in FIG. 1), in accordance with the present invention.

FIG. 3 is a schematic diagram illustrating a more detailed example of a wearable device 11a/12a in accordance with embodiments of the present invention. In some embodiments, the wearable device 12a may be a wearable computer such as a so-called smartwatch, an optical head-mounted computer, an in-ear device, etc.

As depicted, wearable device 12a may include one or more biometric sensors 31. The biometric sensors 31 (such as those described above) may capture physiological data. The wearable device 12a may include a display 32, for example, a touchscreen display, for displaying a user interface with which the wearer may interact with wearable device 12a. The wearable device 12a may further include one or more radios 33 for communicating with the smartwatch device 12b and/or the central server 13. Exemplary radios 33 include a Bluetooth radio, a WiFi radio, and/or a cellular radio such as a Long-Term Evolution (LTE) radio. The wearable device 12a may additionally include a processor 34, and other components (not depicted) for performing the above-described functions. A few (non-limiting) examples of such other components that may be present within or enclose the wearable device 12 include, a memory, one or more buttons or controls, a battery or other power source, and a case/strap for enclosing the various components and keeping them in good contact with the user. The biometric sensors 31 may include various other probes, sensors, electrodes, etc. In some embodiments, such other probes, sensors, electrodes, etc., can integral with the case and held in contact with the wearer's skin by the case/strap and/or attach elsewhere to the wearer's body (and communicate with the device 12a via wire or wireless connection).

Figure 4:
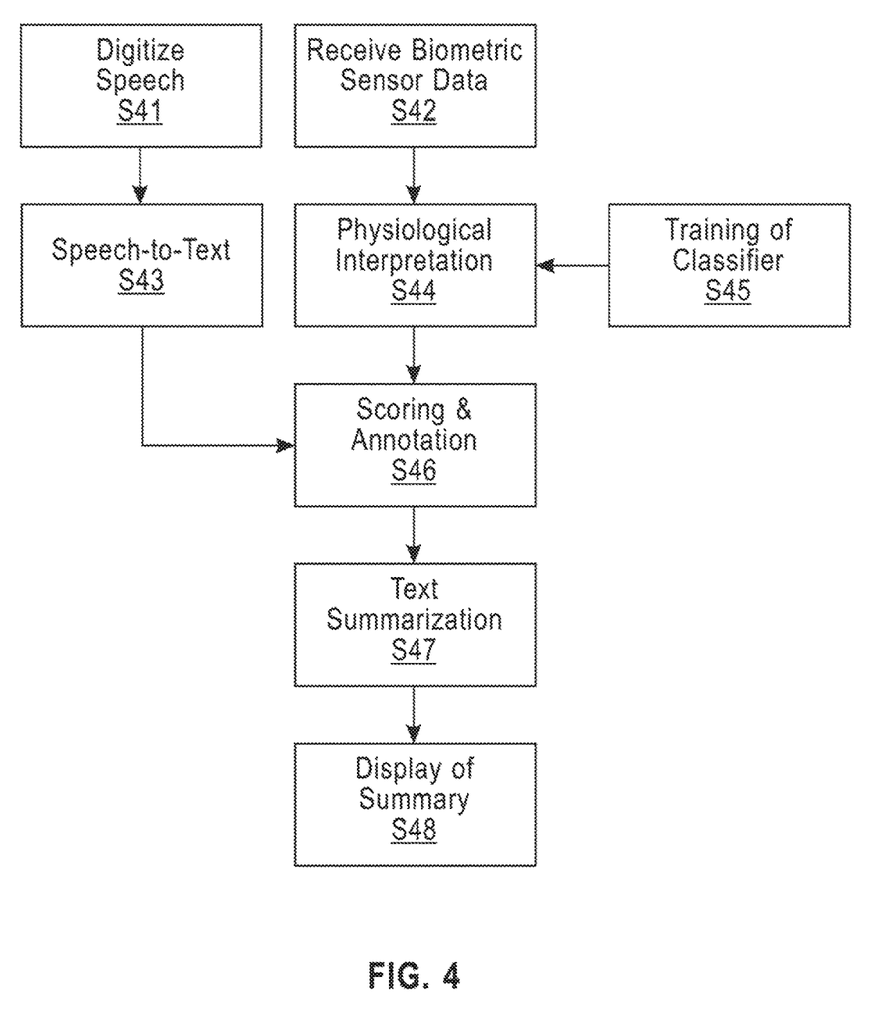
FIG. 4 is a flow chart illustrating a method in accordance with exemplary embodiments of the present invention.

FIG. 4 is a flow chart illustrating a method for performing automated summarization of textual transcripts, according to exemplary embodiments of the present invention. Further to the examples described above, when a presenter is orally delivering a presentation to an audience of participants, in step 41 (S41), the speech of the presenter may be digitized, for example, using a microphone and an analogue-to-digital converter. The digitized speech may then be converted from speech-to-text using one or more approaches for speech recognition (S43). The result of the speech recognition and conversion is a textual transcript. As part of the speech-to-text process (S43), the textual transcript may be time-stamped. The time stamping may be performed either continuously or for discrete passages within the textual transcript. The textual transcript may be divided into passages, which may be individual words, phrases, sentences, paragraphs, etc., as part of the speech-to-text process (S43).

In parallel with the speech digitization (S41), in step 42 (S42) biometric sensor data can be captured/received. As described above, the biometric sensor data may include physiological data captured from wearable and/or remote devices. By way of example only, such physiological data may include one or more of temperature, skin conductivity, heart rate (e.g. pulse), blood pressure, neural oscillations, blood oxygen levels, respiration rate, etc. and/or data from appropriately located sensors, such as video cameras, temperature scanners, humidity sensors, mechanical odor detectors, etc. that may be able to capture information remotely and/or for groups of people at the same time.

In step 44 (S44), the physiological data obtained undergoes physiological interpretation. Physiological interpretation may be performed using a set of rules, as described above.

In some embodiments, in step 45 (S45) a distinguishing classifier that may be trained, using machine learning, during a training step in which training participants whose physiological data is being acquired may be asked to characterize their emotional state/state of engagement.

Referring again to S44, the physiological interpretation (S44) transforms the received physiological data, e.g., biometric sensor data, etc. into an indication of the emotional state/state of engagement of the presenter and/or the various participants.

In step 46 (S46), such indications of the emotional state/state of engagement may be correlated with and used to annotate the corresponding passages of textual transcript. By way of example only, by time stamp information associated with the textual transcript and the biometric sensor data can be used to facilitate such correlation and annotation. The annotated textual transcript may include the text of the speech-to-text step, the time stamps, and the interpretation of the presenter's and/or participant(s)' emotional state/state of engagement.

In some embodiments, in S46, such interpretation may be represented as an engagement score. In some embodiments, the engagement score may be a single value, for example, a value of between "0" and "I", where 1 may represent a maximum engagement by the presenter and all participants, and where 0, may represent a minimum engagement by the presenter and all participants. In some embodiments, a computation of the score may give a weight to the presenter vs. the participants, and reflect determinations as to what types of emotional markers are indicative of a certain level/quality of engagement. According to one such approach, as mentioned above, an average emotional state/state of engagement for all participants may be weighted equally to an emotional state/state of engagement of the presenter. In some embodiments, the emotional state/state of engagement of the presenter is not considered.

According to other exemplary embodiments of the present invention, the participants may be categorized by demographics, organizational hierarchy, or other methods of differentiation, and the emotional state/state of engagement of each group may be differently weighted. For example, emotional state/state of engagement of a high-ranking executive participant may generally be weighted more heavily than that of an intern or trainee.

In step 47 (S47), the annotated textual transcript is summarized. This summarization may be based on the annotated score alone, or as part of a hybrid approach that weighs the annotated score against other indicators of importance, such as keyword use and sentence structure.

Summarization may be performed, for example, by analyzing relevance/frequency measures, analyzing Hidden Markov Models (HMM), performing centroid bases summarization, etc. The summary may be created based on (e.g., by paraphrasing) the most important (highly scored) passages of the textual transcript.

In some embodiments, the textual summarization may use the annotated score, either alone or supplemented with other factors, with an extraction or abstraction approach. In the case of an extraction approach, passages that have a higher annotated score may be more likely to be used within the concise summary. In the case of an abstraction approach, passages that have a higher annotated score may be more strongly expressed or emphasized within the summary.

Regardless of the specifics of the textual summarization (S47), the generated summary can be displayed in step 48 (S48). The display of the summary may include an electronic transmission/distribution of the summary and/or its rendering on a display, printer, or other external device.

Figure 5:
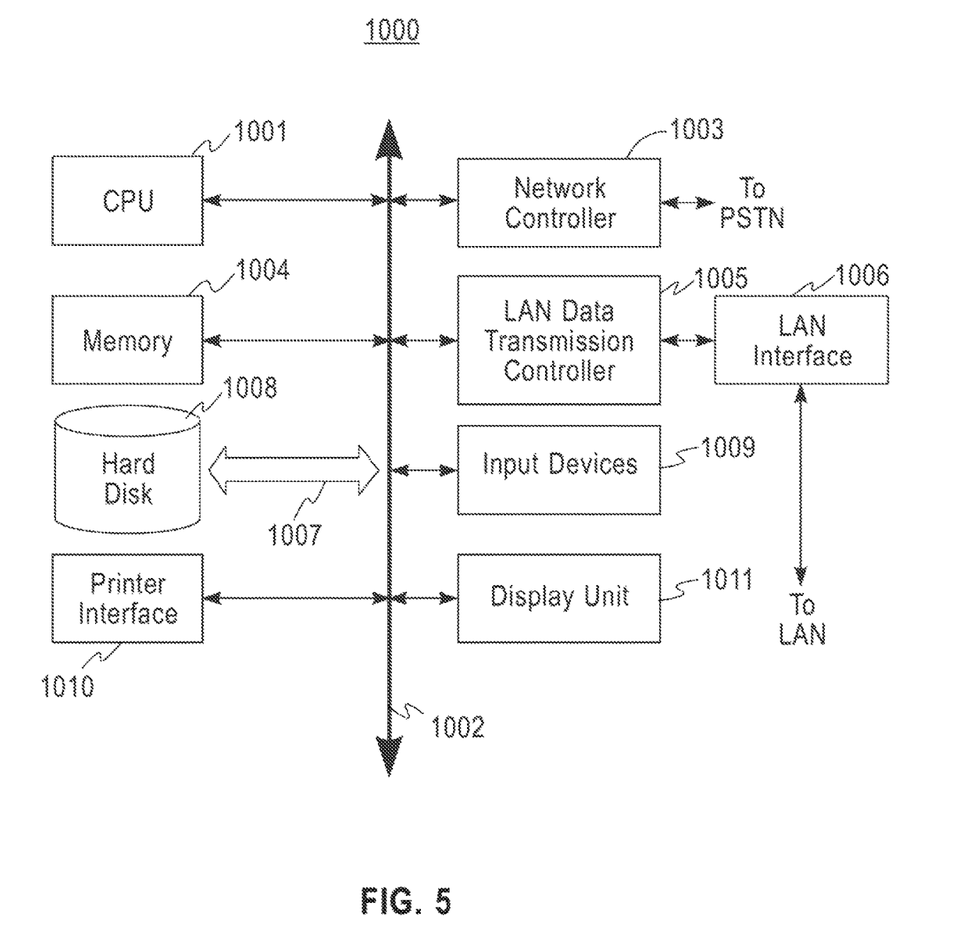
FIG. 5 shows another example of a system in accordance with embodiments of the present invention.

FIG. 5 shows another example of a system in accordance with some embodiments of the present invention. By way of overview, some embodiments of the present invention may be implemented in the form of a software application running on one or more (e.g., a "cloud" of) computer system(s), for example, mainframe(s), personal computer(s) (PC), handheld computer(s), client(s), server(s), peer-devices, etc. The software application may be implemented as computer readable/executable instructions stored on a computer readable storage media (discussed in more detail below) that is locally accessible by the computer system and/or remotely accessible via a hard wired or wireless connection to a network, for example, a local area network, or the Internet.

Referring now to FIG. 5, a computer system (referred to generally as system 1000) may include, for example, a processor e.g., central processing unit (CPU) 1001, memory 1004 such as a random access memory (RAM), a printer interface 1010, a display unit 1011, a local area network (LAN) data transmission controller 1005, which is operably coupled to a LAN interface 1006 which can be further coupled to a LAN, a network controller 1003 for communicating with a Public Switched Telephone Network (PSTN), one or more input devices 1009, for example, a keyboard, mouse etc., and a bus 1002 for operably connecting various subsystems/components. As shown, the system 1000 may also be connected via a link 1007 to a non-volatile data store, for example, hard disk, 1008.

In some embodiments, a software application is stored in memory 1004 that when executed by CPU 1001, causes the system to perform a computer-implemented method described with reference to FIG. 4.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Exemplary embodiments described herein are illustrative, and many variations can be introduced without departing from the spirit of the invention or from the scope of the appended claims. For example, elements and/or features of different exemplary embodiments may be combined with each other and/or substituted for each other within the scope of this invention and appended claims.

What is claimed is:

1. A computer-implemented method for generating an automated summary of a document based on physiological data annotation, comprising:
    digitizing an oral presentation before at least one audience member and performing speech recognition on the digitized oral presentation, using a presenter device, to produce a textual transcript;
    receiving the textual transcript, by a computer in communication with the presenter device over a computer network;
    receiving physiological data from one or more devices used by the at least one audience member that are in communication with the computer over the computer network;
    scoring passages of the textual transcript, by the computer, based on received physiological data;
    automatically creating a summary of the textual transcript, by the computer, in response to said scoring passages of the textual transcript; and
    displaying the created summary on an external device.

2. The computer-implemented method of claim 1, wherein the one or more devices are worn by an audience to the oral presentation.

3. The computer-implemented method of claim 1, wherein the one or more devices are one or more wearable devices.

4. The computer-implemented method of claim 1, wherein the one or more devices include a plurality of biometric sensors.

5. The computer-implemented method of claim 1, wherein the one or more devices includes a smartwatch.

6. The computer-implemented method of claim 1, wherein the physiological data includes physiological data selected from a group consisting of: body temperature, skin conductivity, heart rate, blood pressure, neural oscillations, blood oxygen levels, respiration rate, or pheromone levels.

7. The computer-implemented method of claim 1, further comprising interpreting the received physiological data as a level of emotional excitement/engagement; wherein said scoring of the passages of the textual transcript is performed in response to said interpreting the received physiological data as a level of emotional excitement/engagement.

8. The computer-implemented method of claim 1, wherein passages of the textual transcript having a highest score are represented in the summary.

9. A system for generating an automated summary of a document based on physiological data annotation, comprising:
    a processor;
    a memory, operably coupled to the processor, the memory comprising program instructions that when executed by the processor, cause the system to:
    digitizing an oral presentation before at least one audience member and performing speech recognition on the digitized oral presentation, using a presenter device, to produce a textual transcript;
    receiving the textual transcript, by a computer in communication with the presenter device over a computer network;
    receiving physiological data from one or more devices used by the at least one audience member that are in communication with the computer over the computer network;
    scoring passages of the textual transcript, by the computer, based on received physiological data;
    automatically creating a summary of the textual transcript, by the computer, in response to said scoring passages of the textual transcript; and
    displaying the created summary on an external device.

10. The system of claim 9, wherein the one or more devices are worn by an audience to the oral presentation.

11. The system of claim 9, wherein the one or more devices are one or more wearable devices.

12. The system of claim 9, wherein the one or more devices includes a biometric sensor that is adapted to measure data selected from a group consisting of: body temperature, skin conductivity, heart rate, blood pressure, neural oscillations, blood oxygen levels, respiration rate, or pheromone levels.

13. A computer program product for generating an automated summary of a document based on physiological data annotation, the computer program product comprising a computer readable storage medium having program instructions embodied therewith, the program instructions executable by a computer to cause the computer to:
    digitizing an oral presentation before at least one audience member and performing speech recognition on the digitized oral presentation, using a presenter device, to produce a textual transcript;

receiving the textual transcript, by a computer in communication with the presenter device over a computer network;

receiving physiological data from one or more devices used by the at least one audience member that are in communication with the computer over the computer network;

scoring passages of the textual transcript, by the computer, based on received physiological data;

automatically creating a summary of the textual transcript, by the computer, in response to said scoring passages of the textual transcript; and displaying the created summary on an external device.

14. The computer program product of claim 13, wherein the one or more devices are worn by an audience to the oral presentation.

15. The computer program product of claim 13, wherein the one or more devices include a plurality of biometric sensors.

16. The computer program product of claim 13, wherein the physiological data includes physiological data selected from a group consisting of: body temperature, skin conductivity, heart rate, blood pressure, neural oscillations, blood oxygen levels, respiration rate, or pheromone levels.

17. The computer program product of claim 13, further comprising interpreting the received physiological data as a level of emotional excitement/engagement; wherein said scoring of the passages of the textual transcript is performed in response to said interpreting the received physiological data as a level of emotional excitement/engagement.

\* \* \* \* \*